United States Patent [19]
Takeda et al.

[11] Patent Number: 5,706,811
[45] Date of Patent: Jan. 13, 1998

[54] METHOD AND APPARATUS FOR SETTING REFERENCE POINT FOR ORGANIC MEASUREMENT

[75] Inventors: Tsunehiro Takeda; Hiroshi Endo; Toru Kumagai, all of Tsukuba, Japan

[73] Assignee: Director-General of Agency of Industrial Science and Technology, Tokyo, Japan

[21] Appl. No.: 564,559

[22] Filed: Nov. 29, 1995

[30] Foreign Application Priority Data

Nov. 30, 1994 [JP] Japan ................................ 6-295463

[51] Int. Cl.$^6$ ........................................... A61B 5/055
[52] U.S. Cl. ...................... 128/653.1; 606/130; 128/731
[58] Field of Search .............................. 128/653.1, 731, 128/639, 898, 897; 606/130; 324/260

[56] References Cited

FOREIGN PATENT DOCUMENTS

| | | |
|---|---|---|
| 1-93008 | 6/1989 | Japan . |
| 2-167137 | 6/1990 | Japan . |
| 3-118040 | 5/1991 | Japan . |
| 3-158138 | 7/1991 | Japan . |
| 4-109930 | 4/1992 | Japan . |
| 4-109932 | 4/1992 | Japan . |
| 5-305062 | 11/1993 | Japan . |

*Primary Examiner*—Marvin M. Lateef
*Assistant Examiner*—Shawna J. Shaw
*Attorney, Agent, or Firm*—Frishauf, Holtz, Goodman, Langer & Chick, P.C.

[57] ABSTRACT

An apparatus includes the position determining members for determining the relative position between the reference frame and the head utilizing at least the teeth or external acoustic meatuses and the nose of the head, and the placement members for placing the magnetic field generating elements for MEG and the markers for MRI measurement at the predetermined reference positions on the head by operating the positioning mechanism movably provided on the reference frame. Thus, the reference points for MRI measurement and MEG can be precisely set at the same position with relatively simple operation.

19 Claims, 5 Drawing Sheets

METHOD AND APPARATUS FOR SETTING REFERENCE POINT FOR ORGANIC MEASUREMENT

BACKGROUND OF THE INVENTION

1. Field of the Invention

The present invention relates to a method and an apparatus for setting a reference point for an organic measurement suitable for precisely positioning data obtained by a biomagnetic, such as brain-magnetism, measurement and magnetic resonance imaging (MRI) to be employed in obtaining organic information.

2. Description of the Related Art

Presently MRI or X-ray CT is widely used to noninvasively get the information of organic figure. On the other hand, as a method for obtaining information of the function of organs, it has been known a method to measure variation of a magnetic field due to an organic current and to record the magnetic field thus generated as a Magnetoencephalogram (MEG).

Therefore, an attempt has been made to analyze activity in a brain by predicting an active portion of the brain by combining the organic figure information obtained through MRI with the organic function information obtained through MEG.

Conventionally, since no effective method is available upon such combining, reference points are visually established in an image obtained through MRI relaying upon external acoustic meatuses and a recess of a nasal upper region. On the other hand, in a measurement to obtain MEG, positions are determined by visually observing a nagion and a tragion. Reference points are then established by fitting magnetic field generating elements on the positions thus determined. Then, combining of both data is performed on the basis of the reference point thus established.

However, in such conventional combining method, since the reference points are established by visual observation or the fitting positions of the magnetic field generating element determined visually, it is inevitable to cause an error to the extent of several mm upon combining of both data.

SUMMARY OF THE INVENTION

Therefore, it is an object of the present invention to solve the problem as set forth above and to provide a method and an apparatus for setting a reference point for organic measurement which can precisely position data obtained through MRI and data of MEG and thus enables analysis of brain activity with high reliability.

In order to accomplish the above-mentioned and other objects, according to one aspect of the invention, a method for setting a reference point for organic measurement comprises the steps of:

determining a relative position between a reference frame and a human head utilizing at least teeth in the head; and placing a magnetic field generating element for MEG and a marker for MRI measurement at a predetermined reference position on the head by operating a positioning mechanism movably provided on the reference frame.

With the foregoing construction according to the first aspect of the reference point setting method according to the invention, since the relative position between the reference frame and the head is determined utilizing at least the teeth, and respectively one or more the magnetic field generating elements for MEG and the markers for MRI measurement are placed at one or more the predetermined reference positions on the head by operating the positioning mechanism movably provided on the reference frame, the reference points for MRI measurement and MEG can be precisely set at the same position with relatively simple operation. Therefore, it permits highly reliable analysis of brain activity by precisely positioning the data obtained through MRI measurement and the data of MEG.

According to another aspect of the invention, a method for setting a reference point for organic measurement comprising the steps of:

determining a relative position between a reference frame and a human head utilizing at least external acoustic meatuses and a nose of the head; and placing a magnetic field generating element for MEG and a marker for MRI measurement at a predetermined reference position on the head by operating a positioning mechanism movably provided on the reference frame.

In the foregoing construction according to the second aspect of the present invention, since the relative position between the reference frame and the head is determined utilizing at least the external acoustic meatuses and the nose, and respectively one or more the magnetic field generating elements for MEG and the markers for MRI measurement are placed at one or more predetermined reference positions on the head by operating the positioning mechanism movably provided on the reference frame, the reference points for MRI measurement and MEG can be precisely set at the same position with relatively simple operation. Therefore, the reference points for MRI and MEG can be precisely matched in the positions.

In the preferred construction, the magnetic field generating element for MEG is in a form of an annular body having a center hole incorporating a coil therein and the marker for MRI measurement is a smaller diameter cylindrical body with a cone-shaped tip end to be inserted through the center hole of the annular body. Therefore, position matching of the magnetic field generating element and the marker can be easily achieved.

The marker for MRI measurement may contain a water molecule and an anti-washable oily paint. In such case, the mark which cannot be easily erased by water washing, can be formed. In such case, since the magnetic field generating element can be stuck on the marked position, repeated measurement in a short period can be easily performed.

The predetermined reference position of the head may be a nagion and tragions.

According to further aspect of the invention, an apparatus for setting a reference point for organic measurement comprises:

a reference frame;

position determining means for determining a relative position between the reference frame and a human head utilizing at least teeth in the human head;

a positioning mechanism movably provided on the reference frame; and placement means provided in the positioning mechanism for placing a magnetic field generating element for MEG and a marker for MRI measurement at a predetermined reference position on the head.

With the further aspect of the invention, since the apparatus includes the position determining means for determining the relative position between the reference frame and the head utilizing at least the teeth, the positioning mechanism movably provided on the reference frame and the placement means for placing the magnetic field generating elements for MEG and the markers for MRI measurement at the predetermined reference positions on the head provided in the positioning mechanism, the reference points for MRI measurement and MEG can be precisely set at the same position with relatively simple construction.

In the preferred construction, the position determining means comprises a biting piece member fixed on the reference frame and bitten between the upper and lower teeth, and a chin fitting member, a head top fitting member and head side fitting members provided on the reference frame for relative movement. According to the preferred construction, the position determining means comprises the biting piece member fixed on the reference frame to be bitten between the upper and lower teeth, the chin fitting member provided on the reference frame for relative motion relative to the latter, and the head top fitting member and the head side fitting members. Thus, the relative position between the reference frame and the head can be relatively easily determined.

The biting piece member may have a ridge to be engaged between adjacent individual teeth in one of upper and lower teeth. Since the biting piece member has a ridge to be engaged between adjacent individual teeth in one of the upper and lower teeth, the relative position between the reference frame and the head can be precisely determined.

According to a still further aspect of the invention, an apparatus for setting a reference point for organic measurement comprising:

a reference frame;

position determining means for determining a relative position between the reference frame and a human head utilizing at least external acoustic meatuses and a nose in the human head;

a positioning mechanism movably provided on the reference frame; and placement means provided in the positioning mechanism for placing a magnetic field generating element for MEG and a marker for MRI measurement at a predetermined reference position on the head.

According to the still further aspect of the present invention, since the apparatus comprises the position determining means determining the relative position between the reference frame and the head utilizing at least the external acoustic meatuses and the nose, and the placement means for placing the magnetic field generating elements for MEG and the markers for MRI measurement at the predetermined reference positions on the head by operating the positioning mechanism movably provided on the reference frame, the reference points for MRI measurement and MEG can be precisely set at the same position with relatively simple operation.

In the preferred construction, the position determining means comprises abutting members provided on the reference frame to be pressed onto the acoustic meautses, a light emitter and a light sensor members provided at opposite sides of the reference frame, and a chin fitting member, a rear head fitting member and head side fitting members provided on the reference frame for relative movement.

Since the position determining means comprises abutting members provided on the reference frame to be pressed onto the external acoustic meatuses, light emitting and sensing devices provided at opposite sides of the reference frame, the chin fitting member, the rear head portion fitting member and the head side fitting members provided on the reference frame for relative movement, the reference points for MRI measurement and MEG can be precisely repeatedly set at the same position with relatively simple operation.

BRIEF DESCRIPTION OF THE DRAWINGS

The present invention will be understood more fully from the detailed description given herebelow and from the accompanying drawings of the preferred embodiment of the invention, which, however, should not be taken to be limitative to the present invention, but are for explanation and understanding only.

In the drawings:

FIGS. 2A to 2C are partial enlarged views, in which FIG. 2A is a perspective view showing a condition where a biting piece member is bitten between teeth, FIG. 2B shows a side elevation of the biting piece member in the condition of FIG. 2A, and FIG. 2C is a section of the biting piece member;

DESCRIPTION OF THE PREFERRED EMBODIMENT

A preferred apparatus for implementing a method for setting a reference point for organic measurement according to the present invention will be discussed hereinafter in detail in terms of a preferred embodiment illustrated in the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to unnecessary obscure the present invention.

Figure 1:
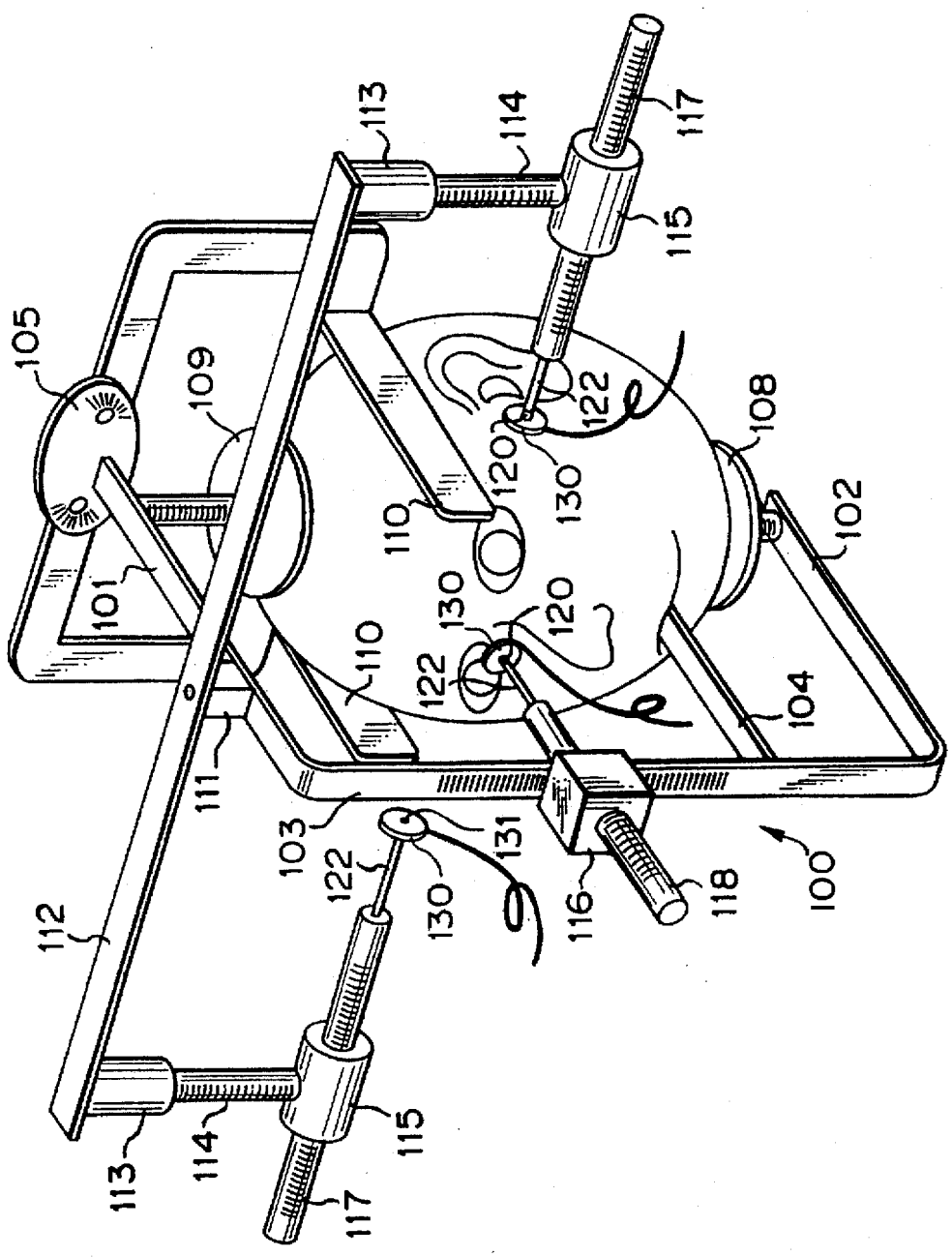
FIG. 1 is a perspective view showing one embodiment of a reference point setting apparatus for organic measurement according to the present invention.
Figure 2A:
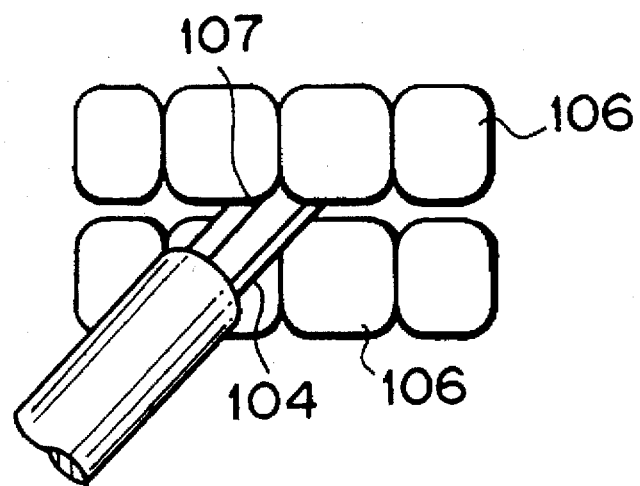
Figure 2B:
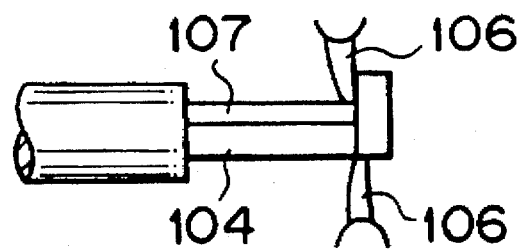
Figure 2C:
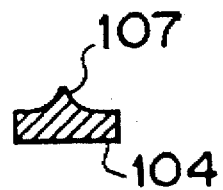

In the first embodiment of a reference point setting apparatus for organic measurement according to the present invention, as illustrated in FIGS. 1 and 2A–2C, reference numeral 100 denotes a substantially C-shaped reference frame which is basically constructed with an upper frame 101, a lower frame 102 and an intermediate frame 103 connecting the upper and lower frames to each other, the reference frame 100 having a biting piece member 104 fixedly provided on the intermediate frame and extending substantially in parallel to the upper and lower frames and a supporting member 105 fixed to a tip end of the upper frame 101 in perpendicular orientation thereto. The biting piece member 104 is bitten between upper and lower teeth 106, as shown in FIGS. 2A–2C and has a ridge 107 engaging between individual teeth of at least one of upper and lower teeth 106.

Furthermore, on the reference frame 100, as a position determining means for determining relative position to a head, a chin fitting member 108 which is provided on the lower frame 102 for movement in the vertical direction relative to a chin, a head top fitting member 109 which is provided on the upper frame 101 for movement in the vertical direction relative to the head, two head side fitting members 110 provided on the support member 105 in a pivotal fashion for relative movement in left and right direction, are provided. These members are fixed by an appropriate fixing means (not shown) after determining respective positions.

Furthermore, as a positioning mechanism provided on the reference frame 100 in a movable fashion, in the shown embodiment, a support base 111 is provided on the upper frame in a movable fashion fore and aft. The support base 111 carries a laterally extending support arm 112 in pivotal fashion. At opposite ends of the support arm 112, first thread receptacle members 113, 113 are rigidly fixed. The first thread receptacle members 113, 113 vertically movably support threaded shafts 114, 114 carrying second thread receptacle members 115, 115 at the lower ends. On the other hand, on the intermediate frame 103, a third thread receptacle member 116 is provided in a vertically movable fashion. The support base 111, the second and third thread receptacle members 115 and 116 are permitted fine positioning relative to the reference frame 100 by means of micrometers. Also, by reading values of scales, respective positions of the support base 111, the second and third thread receptacle members 115 and 116 can be reproduced.

As placement means for positioning magnetic field generating elements for MEG and markers for MRI measurement at predetermined reference positions on the head, on the positioning mechanism, second threaded shafts 117 threadingly engaged with the second thread receptacle members 115 for movement in the lateral direction, and a third threaded shaft 118 threadingly engaged with the third thread receptacle member 116 for movement in the back and forth direction are provided. The second and third threaded shafts 117 and 118 are also permitted fine positioning relative to the positioning mechanism by means of micrometers. Furthermore, the positions of the second and third threaded shafts 117 and 118 can be reproduced by read values of scales. On a tip end of each of the second and third threaded shafts 117 and 118, a support shaft 122 which mounts a marker 120 for MRI measurement, which marker is formed with a cylindrical body having a small diameter and a sharpened tip, is detachably supported. The marker 120 for MRI measurement is made of a substance containing moisture, such as a liquid similar to a body fluid.

On the other hand, reference numeral 130 denotes a magnetic field generating element for MEG. In the shown embodiment, it incorporates a coil and is formed into an annular body having a center hole 131 which has a substantially equal internal diameter to the external diameter of the marker 120 for MRI measurement.

A manner for setting reference points employing the apparatus constructed as set forth above will be discussed hereinafter.

At first, the biting piece member 104 of the reference frame 100 is bitten between the upper and lower teeth of a subjective person for temporarily positioning the reference frame 100. In the shown embodiment, the ridge 107 is formed for engagement between upper two central teeth for assuring positioning.

After temporary positioning, the relative position between the reference frame 100 and the head portion of the subjective person by means of the position determining means. Namely, the chin fitting member 108 provided on the lower frame 102 in a vertically movable fashion is moved until abutting onto the chin of the subjective person. Subsequently, the head top fitting member 109 provided on the upper frame 101 in a vertically movable fashion is moved until abutting onto the head of the subjective person. Thus, the relative position of the reference frame 100 in the vertical direction is determined. Furthermore, the head side fitting members 110, 110 which are pivotable about the support member 105, and thus are relatively movable in the lateral direction, are pivotally moved until abutting onto both sides of the head of the subjective person. Thus, the lateral relative position of the reference frame 100 is determined. These members are fixed in place by appropriate fixing means after positioning. Then, motion magnitudes and pivoting magnitudes are accurately read as an individual data and can be stored.

Once the relative position between the reference frame 100 and the head is determined, the positioning mechanism movably provided on the reference frame 100 is operated to place the magnetic field generating elements for MEG and the markers for MRI measurement at the predetermined reference positions as discussed later. Namely, the support base 111 provided on the upper frame 101 for movement in the back and forth directions is moved, and also, the support arm 112 pivotally mounted on the support base 111 is pivotally moved so that the position of the support arm 112 relative to the reference frame 100 is adjusted at the position corresponding to the tragion as one of the predetermined reference positions of the head. Furthermore, with respect to the first thread receptacle member 113 provided at opposite ends of the support arm 112, the first threaded shafts 114 having the second thread receptacle members 115 are rotated to adjust the vertical position of the second thread receptacle members 115 corresponding to the tragion.

On the other hand, the third thread receptacle member 116 provided on the intermediate frame 103 in a vertically movable fashion is moved so that the vertical position of the third thread receptacle member 116 is adjusted corresponding to the nasion as another one of the predetermined reference positions. The support base 111 and the second and third thread receptacle members 115 and 116 are permitted fine adjustment relative to the reference frame 100 by means of micrometers. Thus, by the read values of the scales as the individual data of the subjective person, these positions can be precisely reproduced.

When the second thread receptacle members 115 and the third thread receptacle member 116 are positioned at the predetermined positions, the magnetic field generating elements for MEG and the markers for MRI measurement are placed at the tragion and nagion positions of the head by the placement means. Namely, the second threaded shaft 117 mounting the support shaft 122 detachably mounting the marker 120 for MRI measurement formed into the small diameter cylindrical body with the sharpened tip, is rotated. Thus, the tip of the marker 120 of the MRI measurement is placed at the tragion position. On the other hand, in the shown embodiment, the magnetic field generating element 130 formed into the annular body having the center hole 121 having the substantially equal internal diameter to the external diameter of the marker 120 for the MRI measurement, is engaged and held on the marker 120 for MRI measurement. Thus, the magnetic field generating element 130 for MEG is also placed at the tragion position together with the marker 120 for MRI measurement.

On the other hand, similarly, the third threaded shaft 118 mounting the support shaft 122 detachably mounting the marker 120 for MRI measurement formed into the small diameter cylindrical body with the sharpened tip, is rotated.

Thus, the tip end of the marker 120 for MRI measurement is placed at the nasion position. Similarly, the magnetic field generating element 130 for MEG which is mounted on the marker 120 for MRI is placed at the nagion position together with the marker 120 for MRI measurement. The second and third threaded shafts 117 and 118 may also be finely positioned relative to the positioning mechanism by means of micrometers. Also, by the read values of the scales, these positions can be accurately reproduced.

After this placement, the magnetic field generating elements 130 for MEG are stuck on the skin of the subjective person, and the markers 120 for MRI measurement are detached from the support shafts 122. Then, the reference point setting apparatus is removed.

Employing the markers 120 for MRI measurement and the magnetic field generating elements 130 positioned on the tragion and nasion positions in the process as set forth above, respective measurements are performed. When MRI measurement is performed, the marker 120 for MRI measurement containing water molecule and formed in the cylindrical body with the sharpened tip end is picked up as is. Thus, the sharpened tip end can be used as the reference point. On the other hand, when measurement is performed for obtaining MEG, in advance of measurement of variation of the magnetic field due to organic current, power is applied to the magnetic field generating element 130 for MEG and whereby the magnetic field is measured. Thus, the center line position of the annular element, at which the strongest magnetism is generated, namely the same position as that of the tip end of the sharpened tip of the marker 120 for MRI measurement can be employed as the reference point.

Thus, by combining the figure information obtained by MRI measurement and the function information obtained by MEG employing the reference points, data composition can be performed without causing error.

Figure 5A:
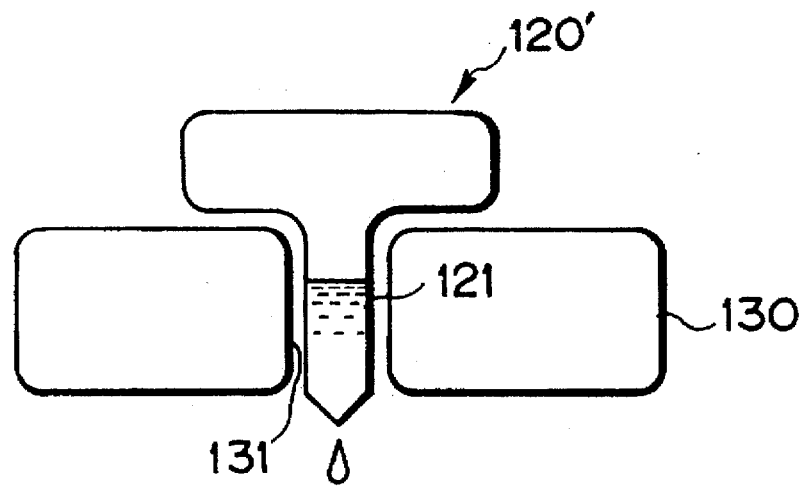
FIGS. 5A and 5B are a sectional view and a perspective view, respectively showing relationship between another embodiment of a marker for MRI measurement to be employed in the present invention and a magnetic field generating element for MEG which is engaged and held by the marker.
Figure 5B:
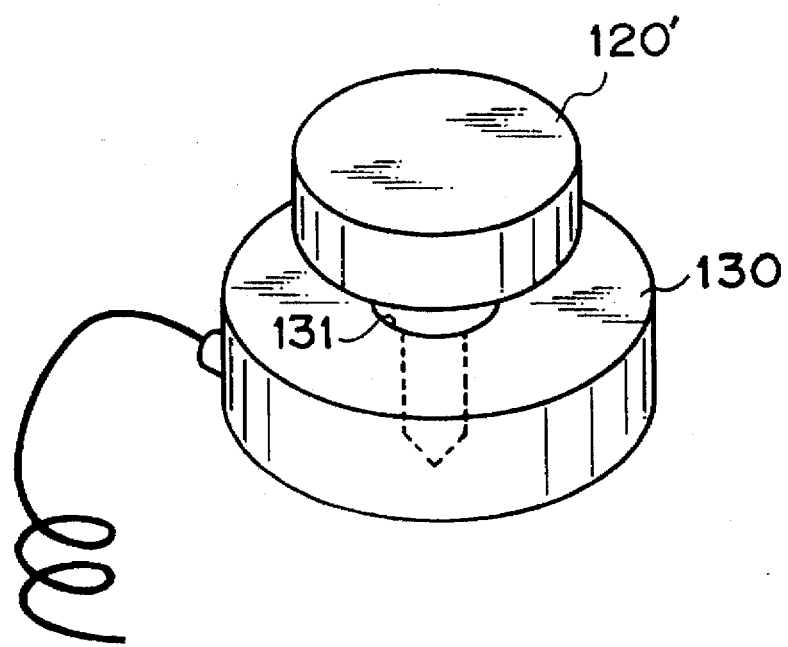

Next, discussion will be given with respect to another embodiment of the marker 120 for MRI measurement with reference to FIG. 5. In the former embodiment, the marker for MRI measurement is simply formed of a substance containing water molecule. In contrast to this, the shown embodiment of marker 120' for MRI measurement contains an anti-washable oily paint 121 in addition to water molecule. Then, the marker 120' for MRI measurement is formed into the small diameter cylindrical body with a cone-shaped tip end similarly to the marker for MRI measurement in the former embodiment. Thus, the marker 120' can be inserted into the center hole 131 of the magnetic field generating element 130 for MEG of the annular configuration. A hole is formed at the tip end of the marker 121' for MRI measurement.

In the marker 120' for MRI measurement, on the tragion and the nagion, the marker 120 for MRI measurement or a support shaft which corresponds to the marker 120 in shape and the magnetic field generating element 130 for MEG are positioned in the same sequential manner as set forth above, and in conjunction therewith, the magnetic field generating element 130 is stuck on the skin and the support shaft 122 (which can be a different bar member only for supporting the magnetic field generating element 130 for MEG without having the marker 120 for MRI measurement, in this embodiment) is retracted. Then, the marker 120' for MRI measurement is inserted into the center hole 131 of the stuck magnetic field generating element 130 for MEG and a mark can be put on the skin of the subjective person by the antiwashable oily paint 121. Since the mark cannot be easily erased by washing or so forth once the mark is put employing the reference point setting apparatus, the mark can be used as reference point indicating the sticking position of the magnetic field generating element 130 for MEG upon next measurement. Therefore, it is convenient to repeatedly perform measurement in a short period. Since the MRI is the measurement for obtaining figure information, the marker 120' becomes unnecessary once the mark position is specified. It should be noted that for the subjective person who hates being put the mark on the skin, the marker 120 B for MRI measurement in the former embodiment may be employed.

Figure 3:
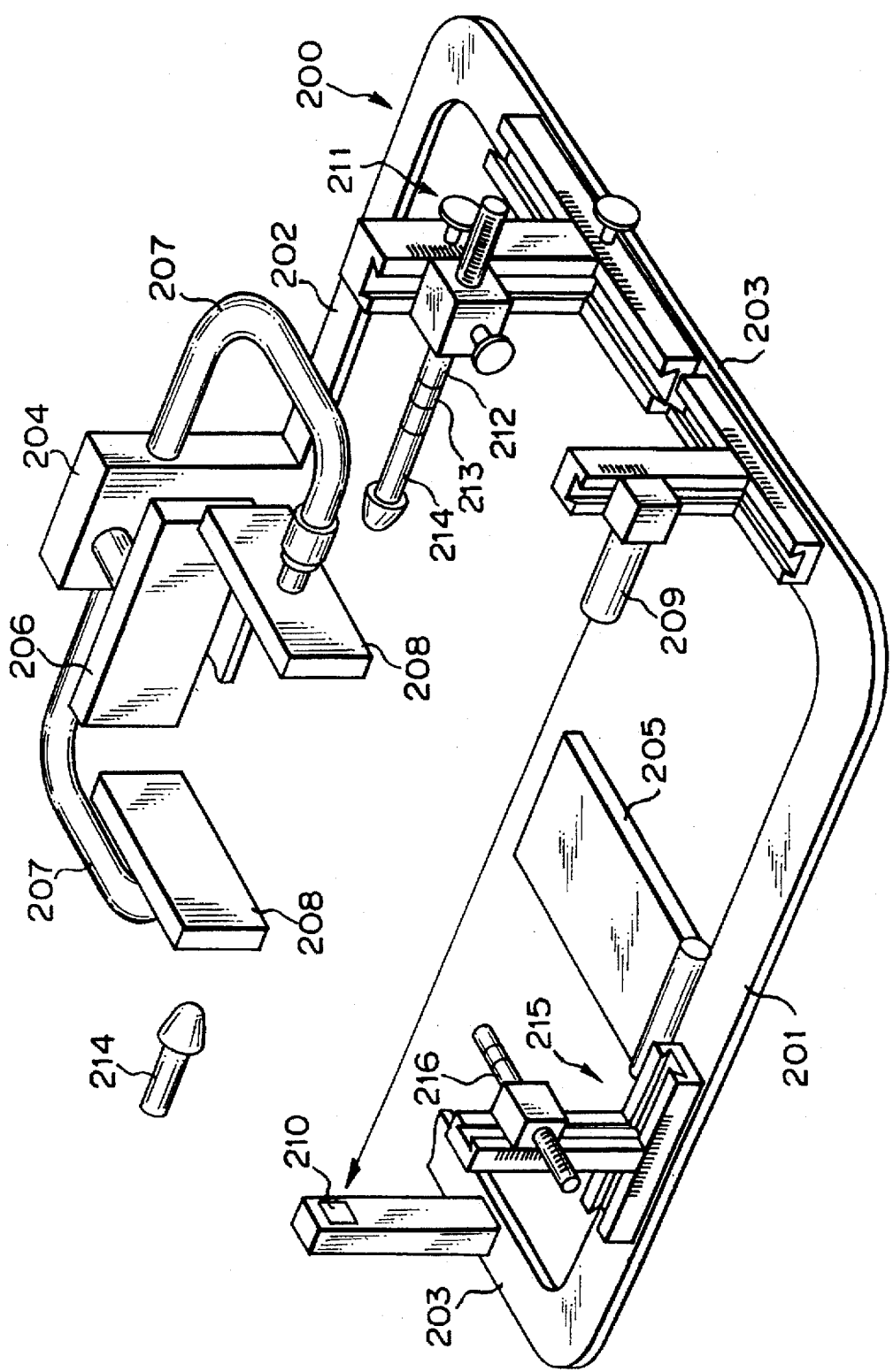
FIG. 3 is a perspective view showing another embodiment of a reference point setting apparatus for organic measurement according to the invention.
Figure 4:
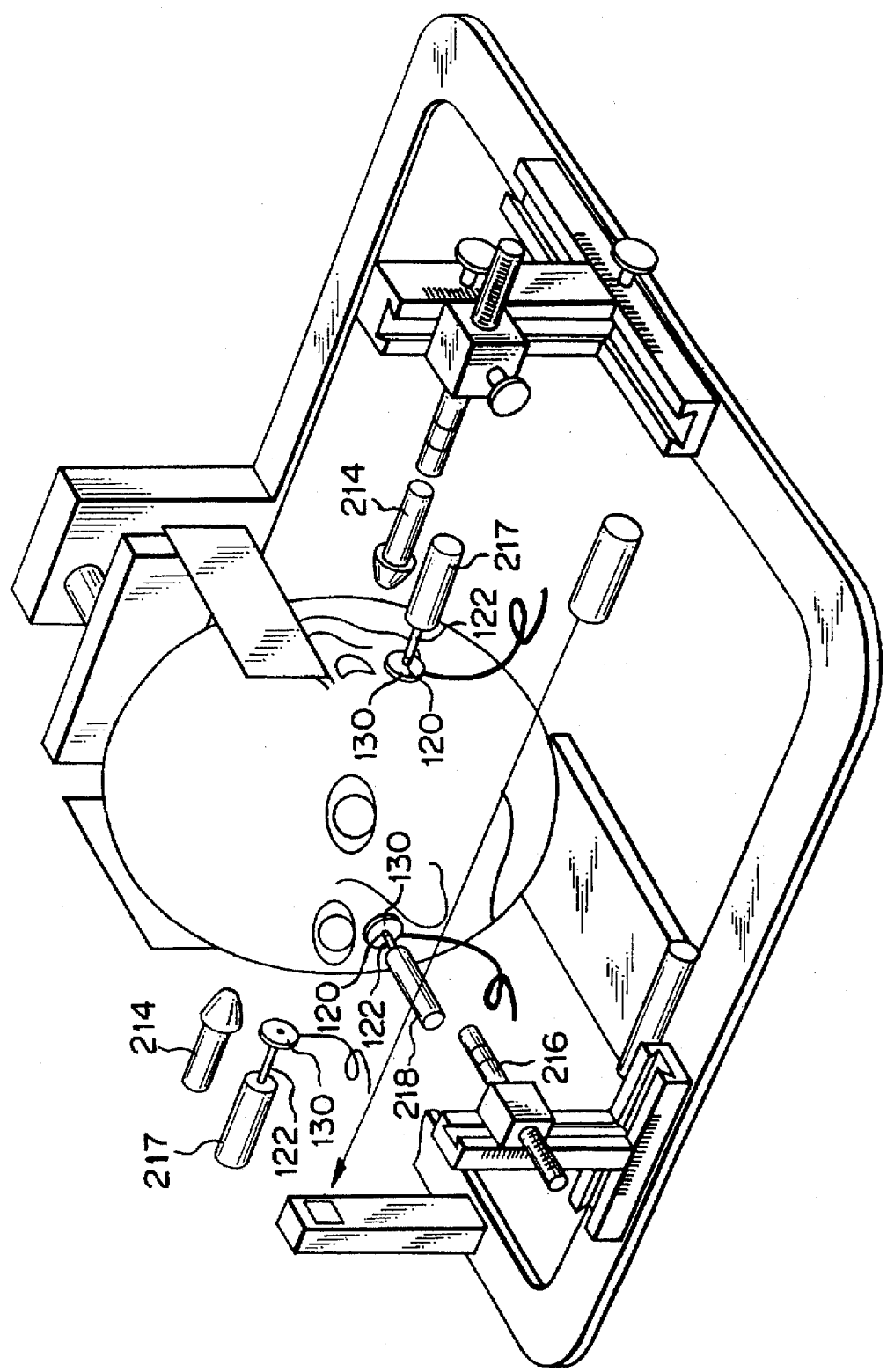
FIG. 4 is a perspective view for explaining manner of use of another embodiment of the reference point setting apparatus of FIG. 3.

Next, another embodiment of the reference point setting apparatus according to the invention will be discussed with reference to FIGS. 3 and 4. The shown embodiment utilizes at least an acoustic meatus and a nose among a head of a human body.

Reference numeral 200 denotes a reference frame having an annular configuration which basically constructed of a front frame 201, a rear frame 202, and two side frames 203,203 connecting the front and rear frames to each other, and a support member 204 rigidly secured on the rear frame 202, perpendicularly. On the reference frame 200, as a position determining means for determining relative position to the head, provided are a chin fitting piece member 205 on the front frame 201 for relative pivotal movement in the vertical direction, a rear head portion fitting member 206 on the support member 204 for relative movement in the back and forth direction, and head side portion fitting members 208, 208 on support arms 207, 207 fixed on the support member 204 for relative movement in the lateral direction. Further provided are a laser generating device 209 as a light emitting device provided on one of the side frames 203 for movement in at least two-dimensional directions for adapting to the difference of the size of the head and the position of the nose of the subjective person, a photo diode array 210 as a photo sensitive device provided at the other side frame 203, and first threaded shaft members 212, 212 held on first XYZ stages 211, 211 with micrometers for movement in three-dimensional directions on both the side frames 203. At the end of the first threaded shaft member 212, an acoustic meatus inserting rod 214 as an abutting member to be pressed onto the acoustic meatus is threadingly engageable through a pressure sensor 213 for measurement of depression pressure interposed therebetween. The tip end of the acoustic meatus inserting rod 214 is formed into cone-shaped configuration, and is fitted thereon a soft pad. It should be noted that respective members set forth above may be fixed in place by appropriate fixing means after positioning.

Also, as one of positioning mechanisms provided on the reference frame 200 in a movable fashion, the first XYZ stages 211, 211 with the micrometers arranged at both sides of the side frames 203,203 in a three-dimensionally movable fashion are employed in common. On the other hand, as the other positioning mechanism, a second XYZ stage 215 with a micrometer is provided on the front frame 201 in a three-dimensionally movable fashion. The second XYZ stage 215 has a second threaded shaft members 216. The first and second threaded shaft members 212 and 216 are permitted fine positioning relative to the reference frame 200 by means of the first and second XYZ stages 211 and 215 with micrometers. The positions of these members can be reproduced by the read values of the scales.

As a placement means provided in the positioning mechanism for placing magnetic field generating elements for MEG and markers for MRI measurement at respective reference positions on the head, first and second mounting bar members 217 and 218 threadingly engaging with the first and second threaded shafts 212 and 216 are provided. On the tip ends of the first and second mounting bar members 217 and 218, the supporting shaft 122 for detachably supporting the marker 120 for MRI measurement which is formed into the small diameter cylindrical body with the cone-shaped tip end, similarly to the former embodiment.

The construction of the magnetic field generating element for MEG is the same as the former embodiment.

Next, discussion will be given for the manner of setting the reference points employing the apparatus constructed as set forth above. In the following discussion for the manner of setting the reference points, the processes are the same as the former embodiment unless specifically mentioned.

At first, by adjusting the position of the first threaded shafts 212 on the first XYZ stage 211, the soft pads on the acoustic meatus inserting rods 214 threaded thereon is gradually inserted into both external acoustic meatuses of the subjective person to perform positioning in the lateral direction to restrict freedom of rotation of the head about a vertical axis. Thus, the reference frame 200 is temporarily positioned.

Then, after temporary positioning, the relative position of the reference frame 200 and the head is determined by means of the position determining means. Namely, the chin fitting member 205 provided on the front frame 201 in a vertical movable fashion is moved vertically abutting with the chin of the subjective person. Then, by depending the position where a laser beam emitted from the laser generating device 209 is partially blocked by the lower end of the nose and thus the detection output of the photo diode array 210 becomes smaller than or equal to a predetermined value, is detected. Thus, the position of the head in the back and forth direction is adjusted. After adjustment, the chin fitting member 205 is fixed in place. Then, the rear head portion fitting member 206 provided on the support member 204 for movement in the back and forth direction is moved until abutting on the rear head portion of the subjective person. Thus, the relative position of the back and forth and vertical direction of the reference frame 200 is determined. Furthermore, the head side portion fitting members 208, 208 provided on the support arms 207 in a laterally movable fashion are moved until abutting onto the both side portions of the head. Thus, the relative position of the reference frame 200 in the lateral direction is determined. After positioning, the members set forth above are fixed in place by means of the appropriate fixing means. The motion magnitude and the pivoting magnitude are accurately read as the individual data and stored.

Once the relative position between the reference frame 200 and the head is determined, the first threaded shaft 212 in the first XYZ stage is adjusted the position for retracting. Thus, the soft pads carried on the acoustic meatus insertion rods 214 are released from both external acoustic meatuses of the subjective person. As a result, deformation of the skin can be removed. Then, the positioning mechanism movably provided on the reference frame 200 is operated so as to place the magnetic field generating elements for MEG and the markers for MRI measurement at respective predetermined reference positions on the head, in the manner as set forth above. Namely, the first threaded shafts 212 of the first XYZ stages 211 which are provided on the side frames 213 for movement in the XYZ directions are moved forward and vertical direction so that the position of the first threaded shafts 212 relative to the reference frame 200 are adjusted to the positions corresponding to the tragions as one of the predetermined reference position on the head.

On the other hand, the second threaded shaft 216 of the second XYZ stage 215 movably provided on the front frame 201 for movement in the XYZ directions is moved in lateral and vertical directions. Thus, the position of the second threaded shaft 216 is adjusted to the position corresponding to the nagion as the other of the predetermined reference positions of the head.

Once the first and second threaded shafts 212 and 216 are positioned at the predetermined positions by means of the positioning mechanism, the magnetic field generating elements for MEG and the markers for MRI measurement are placed at the tragions and nagion on the head by means of the placement means. Namely, first mounting bar members 217 each of which is threadingly engaged with the first threaded shaft 212 and carrying the support shaft 122 supporting the marker 120 for MRI in the small diameter cylindrical body forms with the cone-shaped tip end, are fed to place the markers 120 for MRI measurement at the tip end on the tragion positions. On the other hand, the magnetic field generating elements 130 in the annular configuration are engaged with and carried on the markers 120 for MRI measurement, are also placed at the tragion positions together with the markers 120 for MRI measurement. Similarly, a second mounting bar member 218 which is threadingly engaged with the second threaded shaft 216 and carrying the support shaft 122 supporting the marker 120 for MRI in the small diameter cylindrical body forms with the cone-shaped tip end, is fed to place the marker 120 for MRI measurement at the tip end on the nasion position. The magnetic field generating element 130 in the annular configuration fitted to the marker 120 for MRI measurement is also placed at the nasion position together with the marker 120 for MRI measurement.

The first and second mounting bar members 217 and 218 are permitted fine positioning by means of the first and second XYZ stages 211 and 215 with micrometers, respectively. The positions of the members can be reproduced by the read values of the scales.

Although the invention has been illustrated and described with respect to exemplary embodiment thereof, it should be understood by those skilled in the art that the foregoing and various other changes, omissions and additions may be made therein and thereto, without departing from the spirit and scope of the present invention. Therefore, the present invention should not be understood as limited to the specific embodiment set out above but to include all possible embodiments which can be embodies within a scope encompassed and equivalents thereof with respect to the feature set out in the appended claims.

What is claimed is:

1. A method for setting a reference point for organic measurement, comprising the steps of:

determining a relative position between a reference frame and a human head utilizing at least teeth in the head; and placing a magnetic field generating element for MEG and a marker for MRI measurement at a predetermined reference position on the head by operating a positioning mechanism movably provided on said reference frame, wherein said magnetic field generating element for MEG is in a form of an annular body having a center hole incorporating a coil therein and said marker for MRI measurement is a smaller diameter cylindrical body with a cone-shaped tip end to be inserted through said center hole of said annular body.

2. A method as set forth in claim 1, wherein said marker for MRI measurement contains a water molecule and an anti-washable oily paint.

3. A method as set forth in claim 1, wherein said predetermined reference position of the head comprises a nasion and a tragion.

4. A method for setting a reference point for organic measurement, comprising the steps of:

determining a relative position between a reference frame and a human head utilizing at least external acoustic meatuses and a nose of the head; and placing a magnetic field generating element for MEG and a marker for MRI measurement at a predetermined reference position on the head by operating a positioning mechanism movably provided on said reference frame, wherein said magnetic field generating element for MEG is in a form of an annular body having a center hole incorporating a coil therein and said marker for MRI measurement is a smaller diameter cylindrical body with a cone-shaped tip end to be inserted through said center hole of said annular body.

5. A method as set forth in claim 4, wherein said marker for MRI measurement contains a water molecule and an anti-washable oily paint.

6. A method as set forth in claim 4, wherein said predetermined reference position of the head comprises a nasion and a tragion.

7. An apparatus for setting a reference point for organic measurement, comprising:

a reference frame;

position determining means for determining a relative position between said reference frame and a human head utilizing at least teeth in the human head;

a positioning mechanism movably provided on said reference frame; and placement means provided in said positioning mechanism for placing a magnetic field generating element for MEG and a marker for MRI measurement at a predetermined reference position on the head, wherein said magnetic field generating element for MEG is in a form of an annular body having a center hole incorporating a coil therein and said marker for MRI measurement is a smaller diameter cylindrical body with a cone-shaped tip end to be inserted through said center hole of said annular body.

8. An apparatus as set forth in claim 7, wherein said position determining means comprises a biting piece member fixed on said reference frame and bitten between the upper and lower teeth, and a chin fitting member, a head top fitting member and head side fitting members provided on said reference frame for relative movement.

9. An apparatus as set forth in claim 8, wherein said biting piece member has a ridge to be engaged between adjacent individual teeth in one of upper and lower teeth.

10. An apparatus for setting a reference point for organic measurement, comprising:

a reference frame;

position determining means for determining a relative position between said reference frame and a human head utilizing at least teeth in the human head;

a positioning mechanism movably provided on said reference frame; and placement means provided in said positioning mechanism for placing a magnetic field generating element for MEG and a marker for MRI measurement at a predetermined reference position on the head, wherein said marker for MRI measurement contains a water molecule and an anti-washable oily paint.

11. An apparatus as set forth in claim 7, wherein said predetermined reference position of the head comprises a nasion and a tragion.

12. An apparatus for setting a reference point for organic measurement comprising:

a reference frame;

position determining means for determining a relative position between said reference frame and a human head utilizing at least external acoustic meatuses and a nose in the human head;

a positioning mechanism movably provided on said reference frame; and placement means provided in said positioning mechanism for placing a magnetic field generating element for MEG and a marker for MRI measurement at a predetermined reference position on the head.

13. An apparatus for organic measurement, comprising:

a reference frame;

position determining means for determining a relative position between said reference frame and a human head utilizing at least external acoustic meatuses and a nose in the human head;

a positioning mechanism movably provided on said reference frame, and placement means provided in said positioning mechanism for placing a magnetic field generating element for MEG and a marker for MRI measurement at a predetermined reference position on the head, wherein said position determining means comprises abutting members provided on said reference frame to be pressed onto said external acoustic meatuses, a light emitter and a light sensor provided at opposite sides of said reference frame, and a chin fitting member, a rear head fitting member and head side fitting members provided on said reference frame for relative movement.

14. An apparatus for organic measurement, comprising:

a reference frame;

position determining means for determining a relative position between said reference frame and a human head utilizing at least external acoustic meatuses and a nose in the human head;

a positioning mechanism movably provided on said reference frame; and placement means provided in said positioning mechanism for placing a magnetic field generating element for MEG and a marker for MRI measurement at a predetermined reference position on the head, wherein said magnetic field generating element for MEG is in a form of an annular body having a center hole incorporating a coil therein and said marker for MRI measurement is a smaller diameter cylindrical body with a cone-shaped tip end to be inserted through said center hole of said annular body.

15. An apparatus for organic measurement, comprising:

a reference frame;

position determining means for determining a relative position between said reference frame and a human head utilizing at least external acoustic meatuses and a nose in the human head;

a positioning mechanism movably provided on said reference frame; and placement means provided in said positioning mechanism for placing a magnetic field generating element for MEG and a marker for MRI measurement at a predetermined reference position on the head, wherein said marker for MRI measurement contains a water molecule and an anti-washable oily paint.

16. An apparatus as set forth in claim 13, wherein said predetermined reference position of the head comprises a nasion and a tragion.

17. An apparatus as set forth in claim 14, wherein said predetermined reference position of the head comprises a nasion and a tragion.

18. An apparatus as set forth in claim 15, wherein said predetermined reference position of the head comprises a nasion and a tragion.

19. An apparatus as set forth in claim 10, wherein said predetermined reference position of the head comprises a nasion and a tragion.

* * * * *

UNITED STATES PATENT AND TRADEMARK OFFICE
CERTIFICATE OF CORRECTION

PATENT NO. : 5,706,811

DATED : January 13, 1998

INVENTOR(S) : TAKEDA et al.

It is certified that error appears in the above-identified patent and that said Letters Patent is hereby corrected as shown below:

Title page, Item [56] References Cited, insert:

--U.S. PATENT DOCUMENTS

| | | |
|---|---|---|
| 5,549,616 | 8/27/96 | Schulte et al |
| 4,971,060 | 11/20/90 | Schneider et al |
| 5,594,849 | 1/14/97 | Kuc et al |
| 5,601,569 | 2/11/97 | Pisharodi et al |
| 5,323,777 | 1/28/94 | Ahonen et al |
| 5,397,329 | 3/14/95 | Allen |
| 5,591,175 | 1/7/97 | Juto |
| 5,330,485 | 7/19/97 | Clayman et al |
| 5,469,847 | 11/28/95 | Zinreich et al |
| 5,575,794 | 11/19/96 | Walus et al |
| 5,588,430 | 12/31/96 | Bova et al |
| 5,531,227 | 7/2/96 | Schneider--. |

Under "FOREIGN PATENT DOCUMENTS" insert:

--1,666,093 A1 - 7/30/91 - SU--

Signed and Sealed this

First Day of September, 1998

Attest:

BRUCE LEHMAN

Attesting Officer

Commissioner of Patents and Trademarks